US010155010B1

(12) United States Patent
Perricone

(10) Patent No.: US 10,155,010 B1
(45) Date of Patent: Dec. 18, 2018

(54) BARRIERS FOR GLASS AND OTHER MATERIALS

(71) Applicant: Perricone Hydrogen Water Company, LLC, Meriden, CT (US)

(72) Inventor: Nicholas V. Perricone, Madison, CT (US)

(73) Assignee: Perricone Hydrogen Water Company, LLC, Meriden, CT (US)

( * ) Notice: Subject to any disclaimer, the term of this patent is extended or adjusted under 35 U.S.C. 154(b) by 79 days.

(21) Appl. No.: 15/835,602

(22) Filed: Dec. 8, 2017

Related U.S. Application Data

(63) Continuation of application No. 15/671,397, filed on Aug. 8, 2017.

(51) Int. Cl.
| | |
|---|---|
| *A61K 33/00* | (2006.01) |
| *C01B 3/04* | (2006.01) |
| *B01J 19/12* | (2006.01) |
| *B01J 35/00* | (2006.01) |
| *B01J 21/06* | (2006.01) |
| *A61K 9/00* | (2006.01) |
| *C03C 17/25* | (2006.01) |

(52) U.S. Cl.
CPC ............ *A61K 33/00* (2013.01); *A61K 9/0053* (2013.01); *B01J 19/123* (2013.01); *B01J 19/127* (2013.01); *B01J 21/063* (2013.01); *B01J 35/004* (2013.01); *C01B 3/042* (2013.01); *B01J 2219/0877* (2013.01); *B01J 2219/0892* (2013.01); *B01J 2219/1203* (2013.01); *C03C 17/256* (2013.01); *C03C 2217/212* (2013.01); *C03C 2217/71* (2013.01); *Y02E 60/366* (2013.01)

(58) Field of Classification Search
CPC .................................................. Y02E 60/366
See application file for complete search history.

(56) References Cited

U.S. PATENT DOCUMENTS

| | | | |
|---|---|---|---|
| 3,074,776 A | 1/1963 | Ryan et al. | |
| 3,655,448 A | 4/1972 | Herbert | |
| 3,963,460 A | 6/1976 | Stumpf et al. | |
| 5,382,714 A | 1/1995 | Khachik | |
| 5,648,564 A | 7/1997 | Ausich et al. | |
| 5,803,301 A | 9/1998 | Sato et al. | |
| 5,888,357 A | 3/1999 | Mitsumori et al. | |
| 6,017,599 A | 1/2000 | Sakamoto et al. | |
| 6,173,790 B1 | 1/2001 | Russwurm et al. | |
| 7,189,330 B2 | 3/2007 | Hayashi et al. | |
| 7,560,091 B2 | 7/2009 | Hayashi et al. | |
| 8,309,149 B2 | 11/2012 | Yokoyama | |
| 8,518,225 B2* | 8/2013 | Sumita ................. | B01D 61/025 204/252 |
| 8,574,503 B2 | 11/2013 | Satoh et al. | |
| 8,663,444 B2 | 3/2014 | Nabeshima | |
| 8,852,660 B2 | 10/2014 | Miljkovic | |
| 8,887,625 B2 | 11/2014 | Satoh et al. | |
| 8,974,646 B2 | 3/2015 | Park et al. | |
| 9,050,278 B2 | 6/2015 | Ohta et al. | |
| 9,120,672 B2 | 9/2015 | Satoh et al. | |
| 9,144,581 B2 | 9/2015 | Miljkovic | |
| 9,149,774 B2 | 10/2015 | Satoh et al. | |
| 9,511,331 B2 | 12/2016 | Igarashi | |
| 2002/0162458 A1 | 11/2002 | Farr et al. | |
| 2005/0224996 A1 | 10/2005 | Yoshida | |
| 2007/0017801 A1 | 1/2007 | Fukui et al. | |
| 2007/0158449 A1 | 7/2007 | Hoffmann et al. | |
| 2008/0311225 A1 | 12/2008 | Shiga | |
| 2010/0008849 A1 | 1/2010 | Martin | |
| 2010/0008850 A1 | 1/2010 | Martin | |
| 2010/0111830 A1 | 5/2010 | Boyden et al. | |
| 2010/0163226 A1 | 7/2010 | Zornes | |
| 2010/0233231 A1 | 9/2010 | Labrecque et al. | |
| 2011/0111048 A1 | 5/2011 | Satoh et al. | |
| 2011/0151058 A1 | 6/2011 | Yoshida | |

(Continued)

FOREIGN PATENT DOCUMENTS

| | | |
|---|---|---|
| CN | 101961051 A | 2/2011 |
| CN | 105476480 A | 4/2016 |

(Continued)

OTHER PUBLICATIONS

[No Author Listed], 500ml Drinking Hydrogen Rich Water Generator with built in lithium battery fastest delivery and shipping. Ali Express. Retrieved from https://www.aliexpress.com/item/500ml-Drinking-Hydrogen-Rich-Water-Generator-with-bulit-in-lithium-battery-fastest-delivery-and-shipping/32729940876.html?aff_platform=aaf&cpt=1484687007133&sk=JEYRB2F&aff_trace_key=bc5bdfad4e864ea2910a88ec8daf3271-1484687007133-06041-JEYRB2F. Date accessed: Oct. 25, 2017. 3 pages. [No Author Listed], Applications Vacuum Barrier Corporation. Retrieved from http://vacuumbarrier.com/applications/. Last Accessed: Mar. 6, 2017. 1 page.
[No Author Listed], Blue Mercury Product Information. Retrieved from http://www.bluemercury.co.jp/e/product_introduction.html. Date accessed: Oct. 25, 2017. 1 page.
[No Author Listed], H2 Hydrogen Water Pack. Retrieved from http://www.hydrogenwater-stick.com/. Date accessed: Oct. 25, 2017. 6 pages.
[No Author Listed], Liquid Nitrogen Dosing System: Standard Features. Inline Filling Systems. Retrieved from http://www.fillers.com/liquid-nitrogen-dosing-system/. Date accessed: Mar. 6, 2017. 2 pages.

(Continued)

*Primary Examiner* — Kyle A Purdy
(74) *Attorney, Agent, or Firm* — Wolf, Greenfield & Sacks, P.C.

(57) ABSTRACT

Embodiments described herein generally relate to articles and methods for containing compositions comprising hydrogen gas. In some embodiments, the article comprises a container that comprises glass. In some cases, the container may further comprise $TiO_2$, which may be embedded within the glass, coated on the glass, etc. The container further may contain a composition within the container. In some cases, the composition may comprise dissolved hydrogen gas. Such compositions may be useful, for example, for the treatment of animal and human diseases, for improvement in athletic performance, for the enhancement of the overall health of a subject, or the like.

18 Claims, 1 Drawing Sheet

(56) References Cited

U.S. PATENT DOCUMENTS

| | | |
|---|---|---|
| 2011/0155177 A1 | 6/2011 | Tamura et al. |
| 2011/0274922 A1 | 11/2011 | Yasue et al. |
| 2012/0070540 A1 | 3/2012 | Igarashi |
| 2012/0087990 A1 | 4/2012 | Shiga et al. |
| 2012/0107300 A1 | 5/2012 | Schirripa et al. |
| 2012/0289559 A1 | 11/2012 | Niwa et al. |
| 2013/0043124 A1* | 2/2013 | Park .................. C02F 1/4676 204/263 |
| 2013/0108515 A1 | 5/2013 | Satoh et al. |
| 2014/0010483 A1 | 1/2014 | Shih et al. |
| 2014/0247689 A1 | 9/2014 | Wang et al. |
| 2014/0363361 A1 | 12/2014 | Wang et al. |
| 2015/0104698 A1 | 4/2015 | Fung et al. |
| 2015/0197863 A1 | 7/2015 | Kim et al. |
| 2015/0239760 A1 | 8/2015 | Kim et al. |
| 2015/0284280 A1 | 10/2015 | Huang et al. |
| 2016/0030387 A1 | 2/2016 | Winnicki et al. |
| 2016/0030470 A1 | 2/2016 | Huang et al. |
| 2016/0207765 A1 | 7/2016 | Takehara |
| 2016/0263535 A1 | 9/2016 | Lin |
| 2016/0353782 A1 | 12/2016 | Ruppman |
| 2017/0043932 A1 | 2/2017 | Byun et al. |
| 2017/0080022 A1 | 3/2017 | Levy |

FOREIGN PATENT DOCUMENTS

| | | |
|---|---|---|
| CN | 205312023 U | 6/2016 |
| DE | 3048433 A1 | 7/1982 |
| EP | 0767632 A1 | 4/1997 |
| EP | 2583937 A1 | 4/2013 |
| GB | 1014712 A | 12/1965 |
| GB | 2042398 A | 9/1980 |
| GB | 201111619 A | 5/2013 |
| JP | 8056632 | 3/1996 |
| JP | 2002301483 A | 10/2002 |
| JP | 2004351399 A | 12/2004 |
| JP | 3606466 B1 | 1/2005 |
| JP | 2007238100 A | 9/2007 |
| JP | 2008110342 A | 5/2008 |
| JP | 2008178769 A | 8/2008 |
| JP | 4383317 B2 | 12/2009 |
| JP | 4573904 B1 | 11/2010 |
| JP | 2013126650 A | 6/2013 |
| KR | 100678576 B1 | 10/2005 |
| KR | 20060035663 A | 4/2006 |
| RU | 95115488 A | 9/1997 |
| RU | 123685 U1 | 1/2013 |
| TW | I 316922 B | 10/2005 |
| TW | M 492296 U | 12/2014 |
| WO | WO 2008/029525 A1 | 3/2008 |
| WO | WO 2006/051588 A1 | 5/2008 |
| WO | WO 2008/072615 A1 | 6/2008 |
| WO | WO 2011/038799 A1 | 4/2011 |
| WO | WO 2012/073734 A1 | 6/2012 |
| WO | WO 2014/145443 A2 | 9/2014 |
| WO | WO 2015/133409 A1 | 9/2015 |
| WO | WO 2015/175547 A1 | 11/2015 |

OTHER PUBLICATIONS

[No Author Listed], What happens if you mix water with liquid hydrogen? Quora. Retrieved from https://www.quora.com/What-happens-if-you-mix-water-with-liquid-hydrogen. Date accessed: Oct. 25, 2017. 2 pages.

Cleveland et al., Continuously Infusing Hyperpolarized 129Xe into Flowing Aqueous Solutions Using Hydrophobic Gas Exchange Membranes. J Phys Chem B. Sep. 17, 2009; 113(37): 12489-12499.

Esencan et al., Xenon in medical area: emphasis on neuroprotection in hypoxia and anesthesia. Med Gas Res. Feb. 1, 2013;3(1):4. doi: 10.1186/2045-9912-3-4.

Harris et al., Neuroprotection against traumatic brain injury by xenon, but not argon, is mediated by inhibition at the N-methyl-D-aspartate receptor glycine site. Anesthesiology. Nov. 2013;119(5):1137-48. doi: 10.1097/ALN.0b013e3182a2a265.

Harris, Measuring out fluids microdrop by microdrop. Machine Design. Dec. 7, 2000. 8 pages.

Hiraoka et al., Studies on the properties and real existence of aqueous solution systems that are assumed to have antioxidant activities by the action of "active hydrogen." Journal of Health Sciences. 2004; 50(5):456-465.

Koh et al., Xenon gas as a performance-enhancing drug: doping or just hot air? Cycling Tips. Retrieved from https://cyclingtips.com/2014/03/xenon-gas-as-a-performance-enhancing-drug-doping-or-just-hot-air/. Date accessed: Oct. 25, 2017. 11 pages.

Kurita et al., Measurements of hydrogen permeation through fused silica and borosilicate glass by electrochemical pumping using oxide protonic conductor. Solic State Ionics. 2002;146:101-11.

Nicolson et al., Clinical Effects of Hydrogen Administration: From Animal and Human Diseases to Exercise Medicine. International Journal of Clinical Medicine. Jan. 2016;7(1):32-76.

Taleyarkhan, Modeling & Analysis of Liquid Deuterium—Water Reactions. Oak Ridge National Laboratory. 1995. 10 pages.

Ishibashi et al., Consumption of water containing a high concentration of molecular hydrogen reduces oxidative stress and disease activity in patients with rheumatoid arthritis: an open-label pilot study. Med Gas Res. Oct. 2, 2012;2(1):27. doi: 10.1186/2045-9912-2-27.

Kang et al., Effects of drinking hydrogen-rich water on the quality of life of patients treated with radiotherapy for liver tumors. Med Gas Res. Jun. 7, 2011;1(1):11. doi: 10.1186/2045-9912-1-11.

Verkhovskaya et al., Manufacturing the Technology of Xenon Containing Drinking Water and its Influence on Some Psychophysiological Characteristics of Man. Publicly disclosed on May 25-28, 2016.

U.S. Appl. No. 15/834,262, filed Dec. 7, 2017, Perricone.
U.S. Appl. No. 15/838,820, filed Dec. 12, 2017, Perricone.
U.S. Appl. No. 15/671,391, filed Aug. 8, 2017, Perricone.
U.S. Appl. No. 15/671,397, filed Aug. 8, 2017, Perricone.
U.S. Appl. No. 15/671,403, filed Aug. 8, 2017, Perricone.
U.S. Appl. No. 15/835,621, filed Dec. 8, 2017, Perricone.
U.S. Appl. No. 15/671,465, filed Aug. 8, 2017, Perricone.
U.S. Appl. No. 15/835,636, filed Dec. 8, 2017, Perricone.

* cited by examiner

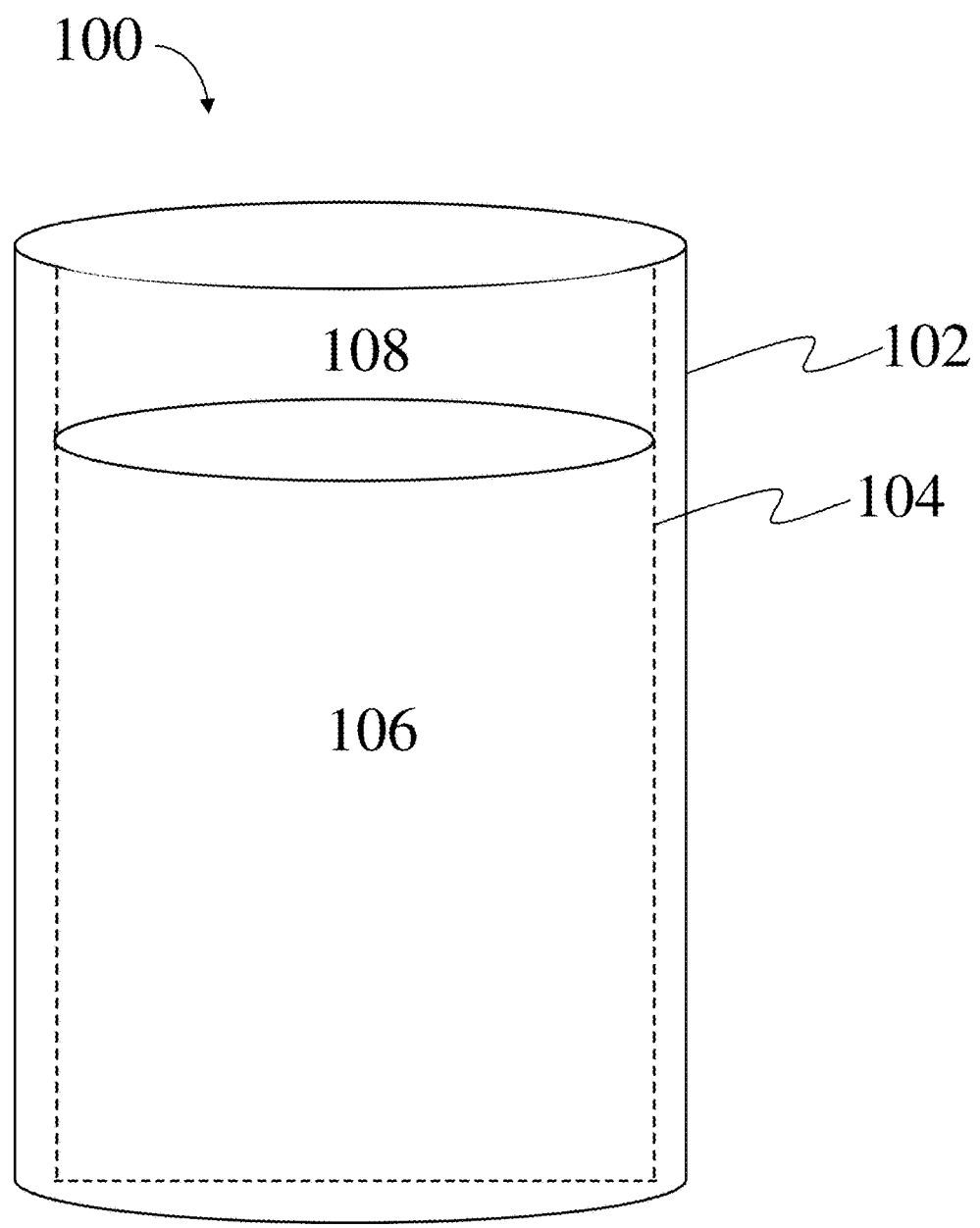

BARRIERS FOR GLASS AND OTHER MATERIALS

RELATED APPLICATIONS

This application a continuation of U.S. patent application Ser. No. 15/671,397, filed Aug. 8, 2017, entitled "Barriers for Glass and Other Materials," by Perricone, which is incorporated herein by reference in its entirety.

FIELD

The present invention generally relates to articles of and methods for containing compositions comprising hydrogen gas.

BACKGROUND

Hydrogen gas ($H_2$) has been shown to have positive effects on animal and human physiology and disease states. $H_2$ can be administered to a subject in the form of, for example, a gas, an infusion, a topical solution, or through the drinking of $H_2$-enriched water. However, due to the small size of $H_2$, containing it in suitable containers has been difficult.

SUMMARY

The present invention generally relates to articles of and methods for containing compositions comprising hydrogen gas (e.g., ingestible compositions such as food and/or drinks; physiological compositions such as blood and plasma; medicinal compositions such as medicine, and/or intravenous solutions; topical compositions such as skin creams and/or topical ointments). The subject matter of the present invention involves, in some cases, interrelated products, alternative solutions to a particular problem, and/or a plurality of different uses of one or more systems and/or articles.

In one aspect, the present invention is generally directed to a container. According to one set of embodiments, the container comprises glass and $TiO_2$ in an amount of at least 10 mass % of the container when empty. In another set of embodiments, the container comprises glass and an agent having a hydrogen permeability of less than less than $10^{-13}$ mol/cm s.

In accordance with another aspect, the present invention is generally directed to a method. In one set of embodiments, the method includes an act of administering a composition to a subject from a container comprising glass and $TiO_2$ in an amount of at least 10 mass % of the container when empty. In some cases, the composition comprises dissolved $H_2$ at a concentration of at least 0.01 ppm.

The method, in another set of embodiments, includes adding a composition to a container comprising glass and $TiO_2$ in an amount of at least 10 mass % of the container when empty, and adding liquid hydrogen to the container.

In another aspect, the present invention encompasses methods of making one or more embodiments described herein, e.g., a glass container for containing compositions comprising hydrogen gas. In still another aspect, the present invention encompasses methods of using one or more of the embodiments described herein, e.g., a glass container for containing compositions comprising hydrogen gas.

Other advantages and novel features of the present invention will become apparent from the following detailed description of various non-limiting embodiments of the invention when considered in conjunction with the accompanying figures.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

The FIGURE shows a schematic drawing illustrating a container comprising glass, a $TiO_2$ coating, and a composition comprising hydrogen gas, according to one set of embodiments.

DETAILED DESCRIPTION

Embodiments described herein generally relate to articles and methods for containing compositions comprising hydrogen gas. In some embodiments, the article comprises a container that comprises glass. In some cases, the container may further comprise $TiO_2$ or other agents to decrease hydrogen permeability, which may be embedded within the glass, coated on the glass, etc. The container further may contain a composition within the container. In some cases, the composition may comprise dissolved hydrogen gas. Such compositions may be useful, for example, for the treatment of animal and human diseases, for improvement in athletic performance, for the enhancement of the overall health of a subject, or the like.

In some cases, the container may be partially or completely made from glass and/or other materials, such as metals (for instance, aluminum, steel, stainless steel, iron, tin, or the like). In certain embodiments, the container may be a bottle, jar, vial, or the like. If glass is used, the glass may be silicate glass, borosilicate glass, Pyrex®, Vycor®, aluminoborosilicate glass, barium aluminoborosilicate glass, soda-lime glass, etc. Other materials may be present within the glass, for example $SiO_2$, $Na_2O$, $Na_2CO_3$, CaO, $CaCO_3$, $Al_2O_3$, $MgCO_3$, $CaMg(CO_3)_2$, NaCl, $Na_2SO_4$, $CaCl_2$, $CaSO_4$, $MgCl_2$, $MgSO_4$, MgO, or other possible additives. In addition, in some embodiments, the glass may be tinted (e.g., to be brown, blue, gray, green, or other colors), by addition of an additive. For example, compounds such as various iron oxides may be added to tint the glass brown or green. In some embodiments, various cobalt oxides may be added to tint the glass blue or gray. According to some embodiments, selenium oxides may be added to tint the glass bronze.

In certain embodiments, the glass may have relatively low hydrogen permeability. For example, the permeability of hydrogen through the glass may be less than less than $10^{-13}$ mol/cm s, less than $10^{-14}$ mol/cm s, less than $10^{-15}$ mol/cm s, less than $10^{-16}$ mol/cm s, less than $10^{-17}$ mol/cm s, less than $10^{-18}$ mol/cm s, less than $10^{-19}$ mol/cm s, less than $10^{-20}$ mol/cm s, etc. Hydrogen permeability values can be experimentally determined, for example, by flowing a stream of hydrogen gas through a permeable system and electrochemically oxidizing the $H_2$ quantifiably to protons ($H^+$).

In some cases, one or more agents may be added to the glass to decrease the permeability of hydrogen gas through the glass, e.g., such that the hydrogen gas has a permeability through the glass as discussed above. The agents may be added to a surface of the glass (inside and/or outside), and/or embedded within the glass (e.g., as the glass is formed), etc. Examples of agents that may be added include, but are not limited to, polymers such as epoxies, oxides such as $TiO_2$, alumina, silica, other inorganic materials, or the like. According to certain embodiments, the agent is an effective Food Contact Substance as approved by the U.S. Food and Drug Administration. The agents may be added, for example, as a film on the glass, sprayed onto the glass, painted onto the glass, stained on the glass, etc.

In one set of embodiments, the agent may include a polymer. Examples of polymers include high-density polyethylene and/or epoxies. Examples of epoxies include, but are not limited to, phenolic, vinyl, acrylic, polyester, polyolefin, organosol, anhydride, amino, oleoresin, or the like. Combinations of these and/or other polymers may also be used in certain embodiments. Additional non-limiting examples of polymers may be found in a patent application filed on Aug. 8, 2017, entitled "Barriers to Hydrogen for Metals and other Materials," by Perricone, which is incorporated herein by reference in its entirety for all purposes.

In some embodiments, the agent may include oxides such as titania ($TiO_2$), alumina, silica, iron, or the like. Without wishing to be bound by any theory, it is believed that the presence of such oxides may result in less space being available for hydrogen to pass through glass, for example, by creating a relatively impermeable layer of material, and/or to decrease the interstices within the glass molecular structure. In some cases, more than one oxide may be used. The oxides may be combined together, or used separately (for example, as separate layers on the glass).

$TiO_2$ may be particularly useful in some embodiments. In some aspects, $TiO_2$ catalyzes the photocatalytic hydrolysis of water. Thus, for example, water contained within liquids or other materials contained within the container may be hydrolyzed to produce $H_2$ and $O_2$, e.g., upon interaction with light such as artificial or natural light. In certain embodiments, the photocatalysis is performed by natural sunlight. In some embodiments, photocatalysis is performed by indoor lighting (e.g., incandescent, fluorescent, LED, etc.), artificial UV light (e.g., from a UV lamp), or the like. In some cases, hydrolysis of water into $H_2$ (and $O_2$) may help to maintain $H_2$ concentrations within the container, or at least partially replenish $H_2$ lost to diffusion out of the container, e.g., through the glass. In some cases, the generated $H_2$ may be able to increase $H_2$ concentrations within the container.

In certain embodiments, the agent to decrease hydrogen permeability may be embedded within the glass, and/or used to coat a surface of the glass. In some embodiments, the agent can be painted, sprayed, coated, stained, etc., on the glass. In some cases, the agent may be applied as a film on the glass. For example, $TiO_2$ or other agents can be applied as a colloidal paste to the glass. If embedded within the glass, the agent can be embedded in the glass, for example, during a synthetic, sintering, welding, and/or other processes.

The agent may be present in any suitable amount or concentration with respect to the container (i.e., when the container is empty). For example, the agent may be present in an amount of at least 1 mass %, at least 5 mass % or at least 10 mass % of the container when empty. For example, according to certain embodiments, the agent is present in an amount of at least 12 mass % of the container when empty, at least 15 mass % of the container when empty, at least 18 mass % of the container when empty, at least 20 mass % of the container when empty. In some cases, the agent may be present in an amount of no more than 25 mass %, no more than 20 mass %, no more than 18 mass %, no more than 15 mass %, no more than 12 mass %, no more than 10 mass %, no more than 8 mass %, no more than 5 mass %, etc. Combinations of any of the above-referenced ranges are also possible. For example, in some embodiments, the agent is present in a range of at least about 10 mass % to about 12 mass % of the container when empty, at last about 10 mass % to about 15 mass % of the container when empty, at least about 10 mass % to about 15 mass % of the container when empty, at least about 10 mass % to about 18 mass % of the container when empty, or at least about 10 mass % to about 20 mass % of the container when empty. Other ranges are also possible.

According to certain embodiments, the agent may be a coating on the entirety of a surface of the container (e.g., an inner and/or outer surface), or a portion thereof. For example, in some embodiments, the agent may coat at least 10%, at least 20%, at least 30%, at least 40%, at least 50%, at least 60%, at least 70%, at least 80%, at least 90%, at least 95%, at least 99%, or 100% by area of a surface of the glass within the container. In some embodiments, the agent coats a glass surface in a range from about 10% to about 20% by area, about 10% to about 30% by area, about 10% to about 40% by area, about 10% to about 50% by area, about 10% to about 60% by area, about 10% to about 70% by area, about 10% to about 80% by area, about 10% to about 90% by area, about 10% to about 95% by area, about 10% to about 99% by area, or about 10% to about 100% by area.

In addition, in some cases, the glass may be tinted. The tinting may be a surface tinting, and/or the tint may be embedded within the glass, e.g., at formation of the glass. For example, brown or green tinting may be embedded within the glass using various iron oxides as an additive during the glass formation process. In certain embodiments, various cobalt oxides may be added to glass as an additive to give it a blue or gray tint. According to some embodiments, selenium oxides can be added to glass to give it a bronze tint. As another example, the tint may be a thin laminate that be installed to the interior and/or exterior of a glass surface. In some cases, the tint can be a coating or a film. In some embodiments, the tint can be made from polyethylene terephthalate. According to some cases, the tint can be applied to the glass as a film and trimmed, or applied as a solution, or synthesized within the glass during a synthetic, sintering, and/or welding process. According to some embodiments, the glass can be at least 1% tinted, at least 2% tinted, at least 5% tinted, at least 10% tinted, at least 15% tinted, at least 25% tinted, at least 50% tinted, at least 75% tinted, at least 90% tinted, at least 95% tinted, or at least 99% tinted (by mass or by volume). In some embodiments, the glass may be no more than 99% tinted, no more than 95% tinted, no more than 90% tinted, no more than 75% tinted, no more than 50% tinted, no more than 25% tinted, no more than 15% tinted, no more than 10% tinted, no more than 5% tinted, etc. by mass or volume. Combinations of the above-referenced ranges are also possible; for example, in some cases, the amount of tinting may be in a range of about 1% to about 2% tinted, about 1% to about 5% tinted, about 1% to about 10% tinted, about 1% to about 15%, about 1% to about 25% tinted, about 1% to about 50% tinted, about 1% to about 75% tinted, about 1% to about 90% tinted, about 1% to about 95% tinted, or about 1% to about 99% tinted (by mass or volume). Other ranges are also possible.

According to some embodiments, the glass can have various degrees of transmittance, i.e., various degrees of transparency or translucency. This can be determined as the amount of light that is able to pass through a material, relative to the incident light. In some cases, at least some of the light may be able to pass through the material without being scattered or distorted (i.e., transparent), although in some cases, the light may pass through the material after being scattered (i.e., translucent). The transmittance of a material may be measured in some embodiments relative to its total transmittance, e.g., as a percentage of the light able to pass through the material, relative to the incident light. The light may be visible light (e.g., 400 to 700 nm), and may be determined using white light at all the wavelengths of the visible spectrum at equal intensity.

The glass forming at least a portion of the container may have varying transmittance dependent upon the material of the glass (including compounds that may provide tinting to the glass) and/or the amount of agent present. For example, according to certain embodiments, the glass may have a transmittance of at least 1%, at least 5%, at least 10%, at least 20%, at least 30%, at least 40%, at least 50%, at least 60%, at least 70%, at least 80%, at least 90%, at least 99%, etc. In some cases, the glass may have a transmittance of no more than 100%, no more than 99%, no more than 95%, no more than 90%, no more than 80%, no more than 70%, no more than 60%, no more than 50%, no more than 40%, no more than 30%, no more than 20%, no more than 10%, or no more than 5%. Combinations of the above-referenced ranges are also possible. For example, the glass may have a transmittance in a range of about 1% to about 5%, about 1% to about 10%, about 1% to about 20%, about 1% to about 30%, about 1% to about 40%, about 1% to about 50%, about 1% to about 60%, about 1% to about 70%, about 1% to about 80%, about 1% to about 90%, or about 1% to about 99%, etc. Other ranges are also possible.

In some cases, the container may contain a composition or other material. For example, as illustrated schematically in the FIGURE, container 100 may comprise a composition (for example, an aqueous solution) 106 stored in container 100. In certain embodiments, the container may be sealed, e.g., to the external atmosphere. For example, in certain embodiments, the container may be sealed such that the composition and/or gases (e.g., hydrogen gas, and/or oxygen gas) that are contained within the container are not able to substantially exit the container. In some cases, the seal may be removable (e.g., such that the composition may be removed from the container and/or orally administered to a subject). For example, in an exemplary embodiment, the container is a bottle and the bottle may be unsealed by removal of a cap of the bottle. In another exemplary embodiment, the container is a can or pouch, and the container may be unsealed by (e.g., via a pull-tab, push-tab, or stay-tab associated with the seal). Upon unsealing of the container, the composition may be ingested (e.g., drunk) by the subject. In some cases, the container may be used for intravenous infusion, or other administration techniques such as those described herein.

In some embodiments, the fluid is present in the container is at or near atmospheric pressure. In some cases, however, the container is able to contain an elevated pressure therein (e.g., a pressure greater than atmospheric pressure). In certain embodiments, the composition is contained within a container at a particular pressure that may be greater than atmospheric pressure. The pressure may be created within the container using any of a variety of gases, including air, nitrogen, carbon dioxide, water vapor, hydrogen gas, or the like, as well as combinations of these and/or other suitable gases. Such gases may be at equilibrium with the composition within the container. In addition, in some cases, one or more of the gases may be present in an amount such that at equilibrium, those gases are dissolved within the composition at saturation concentrations.

For example, in certain embodiments, the container contains a pressure at least 1 psi (1 psi is about 6894.757 Pa), at least 2 psi, at least 3 psi, at least 5 psi, at least 7 psi, at least 10 psi, at least 12 psi, at least 15 psi, at least 18 psi, at least 20 psi, at least 25 psi, at least 30 psi, at least 35 psi, at least 40 psi, or at least 45 psi greater than atmospheric pressure. In some embodiments, the container contains a pressure of less than or equal to 50 psi, less than or equal to 45 psi, less than or equal to 40 psi, less than or equal to 35 psi, less than or equal to 30 psi, less than or equal to 25 psi, less than or equal to 20 psi, less than or equal to 18 psi, less than or equal to 15 psi, less than or equal to 12 psi, less than or equal to 10 psi, less than or equal to 7 psi, less than or equal to 5 psi, less than or equal to 3 psi, or less than or equal to 2 psi greater than atmospheric pressure. Combinations of the above-referenced ranges are also possible (e.g., at least 1 psi and less than or equal to 50 psi greater than atmospheric pressure). Other ranges are also possible.

In some embodiments, the container comprises a gaseous headspace (e.g., a gaseous headspace present within the container). The gaseous headspace may comprise a variety of gases, such as oxygen, air, noble gases, or the like. For example, referring again to the FIGURE, in some cases, container 100 comprises gaseous headspace 108. The container may comprise any suitable amount of headspace within the container. In some embodiments, the headspace occupies greater than or equal to 0.1 vol %, greater than or equal to 0.2 vol %, greater than or equal to 0.25 vol %, greater than or equal to 0.5 vol %, greater than or equal to 0.75 vol %, greater than or equal to 1 vol %, greater than or equal to 1.25 vol %, greater than or equal to 1.5 vol %, greater than or equal to 1.75 vol %, greater than or equal to 2 vol %, greater than or equal to 2.25 vol %, greater than or equal to 2.5 vol %, greater than or equal to 3 vol %, greater than or equal to 3.5 vol %, greater than or equal to 4 vol %, or greater than or equal to 4.5 vol % of the volume contained by the container. In certain embodiments, the headspace occupies less than or equal to 5 vol %, less than or equal to 4.5 vol %, less than or equal to 4 vol %, less than or equal to 3.5 vol %, less than or equal to 3 vol %, less than or equal to 2.5 vol %, less than or equal to 2.25 vol %, less than or equal to 2 vol %, less than or equal to 1.75 vol %, less than or equal to 1.5 vol %, less than or equal to 1.25 vol %, less than or equal to 1 vol %, less than or equal to 0.75 vol %, less than or equal to 0.5 vol %, less than or equal to 0.25 vol %, or less than or equal to 0.2 vol % of the volume contained by the container. Combinations of the above-referenced ranges are also possible (e.g., greater than or equal to 0.1 vol % and less than or equal to 5 vol %). Other ranges are also possible.

For example, in some embodiments, the headspace comprises greater than or equal to 0.00001 vol %, greater than or equal to 0.00005 vol %, greater than or equal to 0.0001 vol %, greater than or equal to 0.0005 vol %, greater than or equal to 0.001 vol %, greater than or equal to 0.005 vol %, greater than or equal to 0.01 vol %, greater than or equal to 0.05 vol %, greater than or equal to 0.1 vol %, greater than or equal to 0.5 vol %, greater than or equal to 1 vol %, greater than or equal to 2 vol %, greater than or equal to 5 vol %, greater than or equal to 10 vol %, greater than or equal to 20 vol %, greater than or equal to 30 vol %, greater than or equal to 40 vol %, greater than or equal to 50 vol %, or greater than or equal to 60 vol % oxygen gas versus the total volume of the headspace. In certain embodiments, oxygen gas is present in the headspace in an amount less than or equal to 70 vol %, less than or equal to 60 vol %, less than or equal to 50 vol %, less than or equal to 40 vol %, less than or equal to 30 vol %, less than or equal to 20 vol %, less than or equal to 10 vol %, less than or equal to 5 vol %, less than or equal to 2 vol %, less than or equal to 1 vol %, less than or equal to 0.5 vol %, less than or equal to 0.1 vol %, less than or equal to 0.05 vol %, less than or equal to 0.01 vol %, less than or equal to 0.005 vol %, less than or equal to 0.001 vol %, less than or equal to 0.0005 vol %, less than or equal to 0.0001 vol %, or less than or equal to 0.00005 vol % versus the total volume of the headspace. Combinations of the above-referenced ranges are also possible (e.g., greater than or equal to 0.00001 vol % and less than or equal to 10 vol %). Other ranges are also possible.

In certain embodiments, the headspace comprises greater than or equal to 0.00001 vol %, greater than or equal to 0.00005 vol %, greater than or equal to 0.0001 vol %, greater than or equal to 0.0005 vol %, greater than or equal to 0.001 vol %, greater than or equal to 0.005 vol %, greater than or equal to 0.01 vol %, greater than or equal to 0.05 vol %, greater than or equal to 0.1 vol %, greater than or equal to 0.5 vol %, greater than or equal to 1 vol %, greater than or equal to 2 vol %, or greater than or equal to 5 vol % hydrogen gas versus the total volume of the headspace. In certain embodiments, hydrogen gas is present in the headspace in an amount less than or equal to 10 vol %, less than or equal to 5 vol %, less than or equal to 2 vol %, less than or equal to 1 vol %, less than or equal to 0.5 vol %, less than or equal to 0.1 vol %, less than or equal to 0.05 vol %, less than or equal to 0.01 vol %, less than or equal to 0.005 vol %, less than or equal to 0.001 vol %, less than or equal to 0.0005 vol %, less than or equal to 0.0001 vol %, or less than or equal to 0.00005 vol % versus the total volume of the headspace. Combinations of the above-referenced ranges are also possible (e.g., greater than or equal to 0.00001 vol % and less than or equal to 10 vol %). Other ranges are also possible.

In one set of embodiments, the composition within the sealed container fills greater than or equal to 50 vol %, greater than or equal to 75 vol %, greater than or equal to 80 vol %, greater than or equal to 85 vol %, greater than or equal to 90 vol %, greater than or equal to 92 vol %, greater than or equal to 95 vol %, greater than or equal to 98 vol %, greater than or equal to 99 vol %, greater than or equal to 99.5 vol %, or greater than or equal to 99.9 vol % of the volume of the sealed container. In some cases, the volume of the composition may be less than or equal to 99.99 vol %, less than or equal to 99.9 vol %, less than or equal to 99.5 vol %, less than or equal to 99 vol %, less than or equal to 98 vol %, less than or equal to 95 vol %, less than or equal to 92 vol %, less than or equal to 90 vol %, less than or equal to 85 vol %, less than or equal to 80 vol %, or less than or equal to 75 vol % of the volume of the sealed container. Combinations of the above-referenced ranges are also possible (e.g., greater than or equal to 50 vol % and less than or equal to 99.99 vol %).

According to certain embodiments, the composition contained in the container comprises hydrogen gas at a concentration of at least 0.01 ppm. For example, in some cases, the composition comprises hydrogen gas at a concentration of at least 0.05 ppm, at least 0.1 ppm, at least 0.2 ppm, at least 0.5 ppm, at least 1.0 ppm, at least 1.5 ppm, at least 1.6 ppm, at least 2 ppm. In some embodiments, the container comprises hydrogen as in a range of concentrations from about 0.01 ppm to about 0.5 ppm, or about 0.01 ppm to about 0.1 ppm, or about 0.01 ppm to about 0.2 ppm, or about 0.01 ppm to about 0.5 ppm, or about 0.01 ppm to about 1.0 ppm, or about 0.01 ppm to about 1.5 ppm, or about 0.01 ppm to 1.6 ppm, or about 0.01 ppm to about 2.0 ppm. Combinations of the above-referenced ranges are also possible. Other ranges are also possible.

In some embodiments, the sealed container described herein are configured to have a relatively long shelf life with respect to the gases contained therein. In certain embodiments, the hydrogen gas and oxygen do not substantially leak from the sealed container for at least 7 days, or longer (e.g., 14 days, 28 days, 56 days, etc.). For example, in some embodiments, greater than or equal to 50 vol %, greater than or equal to 75 vol %, greater than or equal to 80 vol %, greater than or equal to 85 vol %, greater than or equal to 90 vol %, greater than or equal to 92 vol %, greater than or equal to 95 vol %, greater than or equal to 98 vol %, greater than or equal to 99 vol %, greater than or equal to 99.5 vol %, or greater than or equal to 99.9 vol % of the hydrogen gas and/or oxygen gas is present in the sealed container and/or in the headspace 7 days after sealing of the container (including the composition comprising the hydrogen gas and the oxygen gas). In certain embodiments, less than or equal to 99.99 vol %, less than or equal to 99.9 vol %, less than or equal to 99.5 vol %, less than or equal to 99 vol %, less than or equal to 98 vol %, less than or equal to 95 vol %, less than or equal to 92 vol %, less than or equal to 90 vol %, less than or equal to 85 vol %, less than or equal to 80 vol %, or less than or equal to 75 vol % of the hydrogen gas and/or oxygen gas is present in the sealed container and/or in the headspace 7 days after sealing of the container (including within the composition comprising the hydrogen gas and the oxygen gas). Combinations of the above-referenced ranges are also possible (e.g., greater than or equal to 50 vol % and less than or equal to 99.99 vol %). Other ranges are also possible.

The composition comprising hydrogen may be, for example, an ingestible composition including a liquid such as water (or other drinkable liquids), optionally with a variety of additives, such as sugar, electrolytes, caffeine, salt(s), flavoring, vitamins, herbs, amino acids, tea extracts, seed extracts, fruit extracts. The liquid may be any of a variety of drinkable liquids, such as a fruit juice or a juice-like beverage (e.g., powdered drinks such as Crystal Light®, Kool-Aid®, or the like), coffee, tea, a sports drink, an energy drink, soda pop, milk (e.g., cow's milk, goat's milk, sheep's milk, low-fat milk, whole milk, cream, chocolate milk), an alcoholic drink (e.g., mixed alcoholic beverages, wine, beer), or the like.

In some cases, the composition (e.g., an ingestible composition) comprises a food. For example, the composition may include a food such as frozen foods including but not limited to, for example, ice cream, sorbet, gelato, or the like. In some cases, the composition may include a food such as an ingestible colloid, gel, and/or suspension including but not limited to, for example, puddings, custards, and Jell-O®. In an illustrative embodiment, hydrogen gas may be added to a composition such as a food which does not require further heating prior to ingestion (e.g., refrigerated prepared foods, liquids, colloids, gels, and/or suspensions) such that, for example, the hydrogen gas is not boiled out of the composition.

In certain embodiments, the composition comprising hydrogen may be configured to be administered (e.g., orally, intravenously, etc.) to a subject (e.g., in a clinical setting) such as medicinal compositions. For example, the composition may be in the form of an intravenous fluid (e.g., saline, Ringer's lactate). In some cases, the hydrogen gas may be added to compositions such as nasal sprays, ear drops, eye drops, toothpastes, mouthwashes, and/or topical compositions.

In some embodiments, the composition may be configured to be administered to a subject topically (e.g., a topical composition). Non-limiting examples of topical compositions include topical solutions, cosmetics, creams (e.g., steroidal creams, antibiotic creams), foams, pastes, gels, lotions, soaps, jellies (e.g., petroleum jelly), lip balms, shampoos, and ointments.

In certain embodiments, hydrogen gas may be added to a compositions comprising a physiological composition such as blood, plasma, sputum, mucus, urine, and/or sweat. In some embodiments, the physiological composition may be administered to a subject (e.g., hydrogen gas may be added to a physiological composition such as blood and administered to the subject). Advantageously, the addition of hydrogen gas to blood may, for example, aid in the production and/or preservation of the blood.

In some embodiments, one or more additives may be present. Non-limiting examples of additives include sugar, electrolytes, caffeine, salt(s), flavoring, vitamins, herbs, amino acids, tea extracts, seed extracts, fruit extracts, and combinations thereof. The one or more additives may be present in any suitable amount. For example, in some embodiments, the additive is present in the composition in an amount of greater than or equal to 0.1 vol %, greater than or equal to 0.2 vol %, greater than or equal to 0.25 vol %, greater than or equal to 0.5 vol %, greater than or equal to 0.75 vol %, greater than or equal to 1 vol %, greater than or equal to 1.25 vol %, greater than or equal to 1.5 vol %, greater than or equal to 1.75 vol %, greater than or equal to 2 vol %, greater than or equal to 2.25 vol %, greater than or equal to 2.5 vol %, greater than or equal to 3 vol %, greater than or equal to 3.5 vol %, greater than or equal to 4 vol %, or greater than or equal to 4.5 vol % versus the total volume of the composition.

In certain embodiments, the additive is present in the composition in an amount less than or equal to 5 vol %, less than or equal to 4.5 vol %, less than or equal to 4 vol %, less than or equal to 3.5 vol %, less than or equal to 3 vol %, less than or equal to 2.5 vol %, less than or equal to 2.25 vol %, less than or equal to 2 vol %, less than or equal to 1.75 vol %, less than or equal to 1.5 vol %, less than or equal to 1.25 vol %, less than or equal to 1 vol %, less than or equal to 0.75 vol %, less than or equal to 0.5 vol %, less than or equal to 0.25 vol %, or less than or equal to 0.2 vol % versus the total volume of the composition. Combinations of the above-referenced ranges are also possible (e.g., greater than or equal to 0.1 vol % and less than or equal to 5 vol %). Other ranges are also possible.

In some embodiments, the composition comprises hydrogen gas and one or more additives, in the ranges listed above with the remainder of the composition being an ingestible composition, a physiological composition, and/or a topical composition.

In certain embodiments, an ingestible composition is present in an amount of greater than or equal to 90 wt %, greater than or equal to 91 wt %, greater than or equal to 92 wt %, greater than or equal to 93 wt %, greater than or equal to 94 wt %, greater than or equal to 95 wt %, greater than or equal to 96 wt %, greater than or equal to 97 wt %, greater than or equal to 98 wt %, greater than or equal to 99 wt %, greater than or equal to 99.5 wt %, or greater than or equal to 99.9 wt % versus the total composition weight. In some embodiments, the ingestible composition is present in an amount of less than or equal to 99.99 wt %, less than or equal to 99.9 wt %, less than or equal to 99.5 wt %, less than or equal to 99 wt %, less than or equal to 98 wt %, less than or equal to 97 wt %, less than or equal to 96 wt %, less than or equal to 95 wt %, less than or equal to 94 wt %, less than or equal to 93 wt %, less than or equal to 92 wt %, or less than or equal to 91 wt % water versus the total composition weight. Combinations of the above-referenced ranges are also possible (e.g., greater than or equal to 90 wt % and less than or equal to 99.99 wt %, greater than or equal to 95 wt % and less than or equal to 99.99 wt %, greater than or equal to 98 wt % and less than or equal to 99.99 wt %). Other ranges are also possible.

In certain embodiments, ingestible composition is present in an amount of greater than or equal to 90 vol %, greater than or equal to 91 vol %, greater than or equal to 92 vol %, greater than or equal to 93 vol %, greater than or equal to 94 vol %, greater than or equal to 95 vol %, greater than or equal to 96 vol %, greater than or equal to 97 vol %, greater than or equal to 98 vol %, greater than or equal to 99 vol %, greater than or equal to 99.5 vol %, or greater than or equal to 99.9 vol % versus the total volume of the composition. In some embodiments, the ingestible composition is present in an amount of less than or equal to 99.99 vol %, less than or equal to 99.9 vol %, less than or equal to 99.5 vol %, less than or equal to 99 vol %, less than or equal to 98 vol %, less than or equal to 97 vol %, less than or equal to 96 vol %, less than or equal to 95 vol %, less than or equal to 94 vol %, less than or equal to 93 vol %, less than or equal to 92 vol %, or less than or equal to 91 vol % versus the total volume of the composition. Combinations of the above-referenced ranges are also possible (e.g., greater than or equal to 90 vol % and less than or equal to 99.99 vol %, greater than or equal to 95 vol % and less than or equal to 99.99 vol %, greater than or equal to 98 vol % and less than or equal to 99.99 vol %). Other ranges are also possible.

In certain embodiments, a physiological composition is present in an amount of greater than or equal to 90 wt %, greater than or equal to 91 wt %, greater than or equal to 92 wt %, greater than or equal to 93 wt %, greater than or equal to 94 wt %, greater than or equal to 95 wt %, greater than or equal to 96 wt %, greater than or equal to 97 wt %, greater than or equal to 98 wt %, greater than or equal to 99 wt %, greater than or equal to 99.5 wt %, or greater than or equal to 99.9 wt % versus the total composition weight. In some embodiments, the physiological composition is present in an amount of less than or equal to 99.99 wt %, less than or equal to 99.9 wt %, less than or equal to 99.5 wt %, less than or equal to 99 wt %, less than or equal to 98 wt %, less than or equal to 97 wt %, less than or equal to 96 wt %, less than or equal to 95 wt %, less than or equal to 94 wt %, less than or equal to 93 wt %, less than or equal to 92 wt %, or less than or equal to 91 wt % water versus the total composition weight. Combinations of the above-referenced ranges are also possible (e.g., greater than or equal to 90 wt % and less than or equal to 99.99 wt %, greater than or equal to 95 wt % and less than or equal to 99.99 wt %, greater than or equal to 98 wt % and less than or equal to 99.99 wt %). Other ranges are also possible.

In certain embodiments, the physiological composition is present in an amount of greater than or equal to 90 vol %, greater than or equal to 91 vol %, greater than or equal to 92 vol %, greater than or equal to 93 vol %, greater than or equal to 94 vol %, greater than or equal to 95 vol %, greater than or equal to 96 vol %, greater than or equal to 97 vol %, greater than or equal to 98 vol %, greater than or equal to 99 vol %, greater than or equal to 99.5 vol %, or greater than or equal to 99.9 vol % versus the total volume of the composition. In some embodiments, the physiological composition is present in an amount of less than or equal to 99.99 vol %, less than or equal to 99.9 vol %, less than or equal to 99.5 vol %, less than or equal to 99 vol %, less than or equal to 98 vol %, less than or equal to 97 vol %, less than or equal to 96 vol %, less than or equal to 95 vol %, less than or equal to 94 vol %, less than or equal to 93 vol %, less than or equal to 92 vol %, or less than or equal to 91 vol % versus the total volume of the composition. Combinations of the above-referenced ranges are also possible (e.g., greater than or equal to 90 vol % and less than or equal to 99.99 vol %, greater than or equal to 95 vol % and less than or equal to 99.99 vol %, greater than or equal to 98 vol % and less than or equal to 99.99 vol %). Other ranges are also possible.

In certain embodiments, a topical composition is present in an amount of greater than or equal to 90 wt %, greater than or equal to 91 wt %, greater than or equal to 92 wt %, greater than or equal to 93 wt %, greater than or equal to 94 wt %, greater than or equal to 95 wt %, greater than or equal to 96 wt %, greater than or equal to 97 wt %, greater than or equal to 98 wt %, greater than or equal to 99 wt %, greater than or equal to 99.5 wt %, or greater than or equal to 99.9 wt % versus the total composition weight. In some embodiments, the topical composition is present in an amount of less than or equal to 99.99 wt %, less than or equal to 99.9 wt %, less than or equal to 99.5 wt %, less than or equal to 99 wt %, less than or equal to 98 wt %, less than or equal to 97 wt %, less than or equal to 96 wt %, less than or equal to 95 wt %, less than or equal to 94 wt %, less than or equal to 93 wt %, less than or equal to 92 wt %, or less than or equal to 91 wt % water versus the total composition weight. Combinations of the above-referenced ranges are also possible (e.g., greater than or equal to 90 wt % and less than or equal to 99.99 wt %, greater than or equal to 95 wt % and less than or equal to 99.99 wt %, greater than or equal to 98 wt % and less than or equal to 99.99 wt %). Other ranges are also possible.

In certain embodiments, the topical composition is present in an amount of greater than or equal to 90 vol %, greater than or equal to 91 vol %, greater than or equal to 92 vol %, greater than or equal to 93 vol %, greater than or equal to 94 vol %, greater than or equal to 95 vol %, greater than or equal to 96 vol %, greater than or equal to 97 vol %, greater than or equal to 98 vol %, greater than or equal to 99 vol %, greater than or equal to 99.5 vol %, or greater than or equal to 99.9 vol % versus the total volume of the composition. In some embodiments, the topical composition is present in an amount of less than or equal to 99.99 vol %, less than or equal to 99.9 vol %, less than or equal to 99.5 vol %, less than or equal to 99 vol %, less than or equal to 98 vol %, less than or equal to 97 vol %, less than or equal to 96 vol %, less than or equal to 95 vol %, less than or equal to 94 vol %, less than or equal to 93 vol %, less than or equal to 92 vol %, or less than or equal to 91 vol % versus the total volume of the composition. Combinations of the above-referenced ranges are also possible (e.g., greater than or equal to 90 vol % and less than or equal to 99.99 vol %, greater than or equal to 95 vol % and less than or equal to 99.99 vol %, greater than or equal to 98 vol % and less than or equal to 99.99 vol %). Other ranges are also possible.

As mentioned, the composition may be any of a variety of drinkable liquids in various embodiments, such as water, a fruit juice, coffee, tea, a sports drink, an energy drink, soda pop, milk, an alcoholic drink, etc. In some cases, the composition may be in the form of administrable to a subject (e.g., in an intravenous bag or pouch for intravenous delivery such as comprising saline).

In an exemplary embodiment, the container is configured for intravenous delivery of the composition contained therein to a subject and comprises saline (e.g., NaCl dissolved in water). In some such embodiments, the additive is NaCl. In some cases, the composition may be normal saline (i.e. 0.9 wt %/vol % NaCl per total volume of the water present in the composition) and comprises hydrogen gas. In some embodiments, NaCl is present in the composition in an amount of greater than or equal to 0.1 wt %, greater than or equal to 0.2 wt %, greater than or equal to 0.3 wt %, greater than or equal to 0.5 wt %, greater than or equal to 0.7 wt %, greater than or equal to 0.9 wt %, greater than or equal to 1 wt %, greater than or equal to 1.2 wt %, greater than or equal to 1.5 wt %, greater than or equal to 1.7 wt %, or greater than or equal to 2 wt % per total volume of the water present in the composition). In certain embodiments, NaCl is present in the composition in an amount of less than or equal to 2.5 wt %, less than or equal to 2 wt %, less than or equal to 1.7 wt %, less than or equal to 1.5 wt %, less than or equal to 1.2 wt %, less than or equal to 1 wt %, less than or equal to 0.9 wt %, less than or equal to 0.7 wt %, less than or equal to 0.5 wt %, less than or equal to 0.3 wt %, or less than or equal to 0.2 wt %. Combinations of the above-referenced ranges are also possible (e.g., greater than or equal to 0.1 wt % and less than or equal to 2.5 wt %, greater than or equal to 0.7 wt % and less than or equal to 1 wt %). Other ranges are also possible.

In certain embodiments, water is present in the composition in an amount of greater than or equal to 90 vol %, greater than or equal to 91 vol %, greater than or equal to 92 vol %, greater than or equal to 93 vol %, greater than or equal to 94 vol %, greater than or equal to 95 vol %, greater than or equal to 96 vol %, greater than or equal to 97 vol %, greater than or equal to 98 vol %, greater than or equal to 99 vol %, greater than or equal to 99.5 vol %, or greater than or equal to 99.9 vol % versus the total volume of the composition. In some embodiments, the composition comprises less than or equal to 99.99 vol %, less than or equal to 99.9 vol %, less than or equal to 99.5 vol %, less than or equal to 99 vol %, less than or equal to 98 vol %, less than or equal to 97 vol %, less than or equal to 96 vol %, less than or equal to 95 vol %, less than or equal to 94 vol %, less than or equal to 93 vol %, less than or equal to 92 vol %, or less than or equal to 91 vol % versus the total volume of the composition. Combinations of the above-referenced ranges are also possible (e.g., greater than or equal to 90 vol % and less than or equal to 99.99 vol %, greater than or equal to 95 vol % and less than or equal to 99.99 vol %, greater than or equal to 98 vol % and less than or equal to 99.99 vol %). Other ranges are also possible.

Some embodiments of the invention are related to methods of preparing and administering a composition comprising hydrogen gas. For example. certain embodiments are related to a method comprising adding a composition to a container comprising a glass and $TiO_2$ in an amount of at least 10 mass % of the container when empty, and adding $H_2$ to the container in an amount to cause the composition to contain dissolved hydrogen gas in a concentration of at least 0.01 ppm, and sealing the container. Certain embodiments, a method comprising administering a composition to a subject from a container comprising a glass and $TiO_2$ in an amount of at least 10 mass % of the container when empty, wherein the composition comprises dissolved hydrogen gas at a concentration of at least 0.01 ppm.

In certain embodiments, the composition may be orally administered to a subject, (e.g., ingested or drunk by a subject, encapsulated in a pill (e.g., the composition is contained in a capsule such as a gel-capsule)). In certain cases, the subject self-administers the composition. In some such embodiments, the composition may comprise hydrogen gas in an amount of greater than or equal to greater than or equal to 0.01 ppm and less than or equal to 5 ppm and oxygen gas in an amount of greater than or equal to 1 ppm and less than or equal to 20 ppm.

In some embodiments, the composition may be administered intravenously. In some such embodiments, the composition comprises hydrogen gas in an amount of greater than or equal to greater than or equal to 0.01 ppm and less than or equal to 5 ppm and oxygen gas in an amount of greater than or equal to 1 ppm and less than or equal to 20 ppm.

In other embodiments, the composition may be administered rectally. In some such embodiments, the composition comprises hydrogen gas in an amount of greater than or equal to greater than or equal to 0.01 ppm and less than or equal to 5 ppm and oxygen gas in an amount of greater than or equal to 1 ppm and less than or equal to 20 ppm.

In other embodiments, the composition may be administered nasally. In some such embodiments, the composition comprises hydrogen gas in an amount of greater than or equal to greater than or equal to 0.01 ppm and less than or equal to 5 ppm and oxygen gas in an amount of greater than or equal to 1 ppm and less than or equal to 20 ppm.

In other embodiments, the composition may be administered urethrally. In some such embodiments, the composition comprises hydrogen gas in an amount of greater than or equal to greater than or equal to 0.01 ppm and less than or equal to 5 ppm and oxygen gas in an amount of greater than or equal to 1 ppm and less than or equal to 20 ppm.

In one set of embodiments, the composition, prior to administration to a subject, may be contained within a sealed container, e.g., as described herein. For example, the composition may be contained within a can, bottle, jar, pouch, box, bag, or capsule. In some cases, the container may be unsealed just before administration to a subject. For example, the container may be unsealed and then administered to a subject (including self-administration) within 1 hour of unsealing the container, or within 45 minutes, within 30 minutes, within 20 minutes, within 15 minutes, within 10 minutes, within 5 minutes, within 4 minutes, within 3 minutes, within 2 minutes, or within 1 minute of unsealing.

In certain cases, a composition as described herein can be used to treat conditions such as ischemia, e.g., partial ischemia or restriction in blood supply to tissues. For instance, a composition may be administered to a subject to protect neural and/or cardiac function. This may be administered on a regular basis, e.g., as discussed herein, and/or in combination with events such as anesthesia, hypoxia, hypothermia, ischemia, oxygen deprivation, oxygen glucose deprivation, exercise, or other similar conditions in which blood and/or oxygen may be lowered or otherwise altered in a subject, permanently or temporarily. Thus, in various embodiments, a subject having or at risk to conditions such as these may be administered (including self-administration) a composition as discussed herein.

In addition, in some cases, hydrogen may be used to treat oxidative stress diseases and conditions such as smoking, exposure to ultraviolet rays, air pollution, aging, physical or psychological stress, or the aging process, e.g., due to its antioxidant properties.

In one set of embodiments, other gases or other substances may be present within the composition. For example, the composition may comprise one or more noble gases such as xenon. Non-limiting examples of suitable noble gases that may be present in the liquid include helium, neon, argon, krypton, xenon, and radon. In a particular set of embodiments, the noble gas is xenon gas. The noble gas may be substantially dissolved in the composition. For example, the mole fraction solubility of xenon in water at 25° C. and 1 atm is generally $7.890 \times 10^{-5}$. In some embodiments, the amount of noble gas dissolved in the composition is greater than the amount of noble gas that would be dissolved in the composition at the mole fraction solubility of the noble gas in water determined at 25° C. and 1 atm. For example, the composition may be under a pressure greater than 1 atm and/or a temperature greater than 25° C. See, e.g., U.S. Pat. Apl. Ser. Nos. 62/510,102 and 62/510,114, each filed May 23, 2017, each incorporated herein by reference in its entirety.

Accordingly, in one set of embodiments, a composition as described herein is used to treat muscular, neurodegenerative, and/or neuromuscular diseases or other conditions. Thus, in one set of embodiments, the administration of a composition as discussed herein, e.g., comprising hydrogen may be administered to a subject. The subject may be one that is suffering from a muscular, neurodegenerative, or neuromuscular disease, and the subject may exhibit clinical improvement after treatment.

In some cases, administration of a composition as discussed herein may act as a preventative of and/or be used to treat a muscular, neurodegenerative, or neuromuscular disease. In another set of embodiments, a composition as described herein is administered to a subject, e.g., one having or at risk of a muscular, neurodegenerative, or neuromuscular disease. In certain embodiments, the disease is a muscular dystrophy or atrophy (e.g., Becker's muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, oculopharyngeal muscular dystrophy, spinal muscular atrophy, Brown-Vialetto-Van Laere syndrome, Fazio-Londe syndrome). In some embodiments, the disease is a muscular atrophy (e.g., muscle atrophy associated with a cancer, muscle atrophy associated with AIDS, muscle atrophy associated with congestive heart failure, muscle atrophy associated with chronic obstructive pulmonary disease, muscle atrophy associated with renal failure, muscle atrophy associated with severe burns, and muscle atrophy associated with long bed rest). In certain embodiments, the disease is amyotrophic lateral sclerosis. In some embodiments, the disease is Charcot-Marie-Tooth disease, Dejerine-Sottas disease, or Kennedy's disease. In some cases, the disease is Parkinson's disease, Alzheimer's disease, or Huntington's disease. In some embodiments, the subject may be suffering or at risk of neuropathic pain.

In some cases, the subject may be one that already has a muscular, neurodegenerative, or neuromuscular disease. However, in other cases, the subject may not necessarily have a muscular, neurodegenerative, or neuromuscular disease, but may be one that is at risk of developing such a disease. In some embodiments, the subject suffers from a muscular dystrophy. In some embodiments, the subject suffers from muscular atrophy. In some embodiments, the subject is in need of muscle growth or repair. In some embodiments, the subject is in need of enhanced muscle performance.

In some embodiments, compositions described herein may be used for stimulation of vasodilation prior to physical exercise. The composition may be used, for example, prior to a workout at the gym, or before a training or game of any sports. In some embodiments, a composition described herein is administered to a subject prior to physical exercise. In certain embodiments, compositions described herein are administered to provide enhanced muscle performance.

The subject may be a healthy subject, or one who has or is at risk for a muscular or neuromuscular disease, e.g., as discussed herein. In some cases, the subject may be an older subject, e.g., having or at risk of muscle weakening due to age. For example, the subject may be one that is at least 40 years old, at least 50 years old, at least 60 years old, or at least 70 years old.

In another set of embodiments, the present invention is generally directed to preventing and/or reversing cardiovascular disease, such as atherosclerosis, hypertension, high blood pressure, sickle-cell anemia, neointimal hyperplasia, peripheral artery disease, high-density lipoprotein deficiency, etc., e.g., using compositions and methods as discussed herein.

In some embodiments, the subject may be one that exhibits one or more symptoms of atherosclerosis. For example, the subject may have a history or a family history of atherosclerosis, or the subject may exhibit symptoms such as elevated blood pressure (i.e., hypertension), chest pain (angina), sudden numbness or weakness in the arms or legs, difficulty speaking or slurred speech, drooping muscles in the face, leg pain when walking, and/or claudication.

Additionally, in some embodiments, the composition may be applied in conjunction with other types of treatments to a subject, e.g., to treat or prevent arteriosclerosis, hypertension, sickle-cell anemia, etc. Non-limiting examples of such treatments include any one or more of those discussed herein. These may be occur, e.g., simultaneously or sequentially, in various embodiments.

Examples of other treatments of cardiovascular diseases include, but are not limited to, nitrates (e.g., nitroglycerine, isosorbide, etc.), beta blockers (e.g., atenolol, metoprolol, nadolol, oxprenolol, pindolol, propranolol, timolol, etc.), alpha blockers (e.g., doxazosin, phentolamine, indoramin, phenoxybenzamine, prazosin, terazosin, tolazoline, etc.), calcium channel blockers (e.g., amlodipine, aranidipine, azelnidipine, barnidipine, benidipine, cilnidipine, clevidipine, isradipine, efonidipine, felodipine, lacidipine, lercanidipine, manidipine, nicardipine, nifedipine, nilvadipine, nimodipine, nisoldipine, nitrendipine, pranidipine, diltiazem, mibefradil, bepridil, fluspirilene, fendiline, etc.), or the like.

Additional examples of treatments include, but are not limited to, loop diuretics (e.g., bumetanide, ethacrynic acid, furosemide, torsemide, etc.), thiazide diuretics (e.g., epitizide, hydrochlorothiazide, chlorothiazide, bendroflumethiazide, etc.), thiazide-like diuretics (e.g., indapamide, chlorthalidone, metolazone, etc.), potassium-sparing diuretics (e.g., amiloride, triamterene, spironolactone, etc.), beta blockers (e.g., atenolol, metoprolol, nadolol, oxprenolol, pindolol, propranolol, timolol, etc.), alpha blockers (e.g., doxazosin, phentolamine, indoramin, phenoxybenzamine, prazosin, terazosin, tolazoline, etc.), mixed alpha and beta blockers (e.g., bucindolol, carvedilol, labetalol, etc.), dihydropyridines (e.g., amlodipine, felodipine, isradipine, lercanidipine, nicardipine, nifedipine, nimodipine, nitrendipine, etc.), non-dihydropyridines (e.g., diltiazem, verapamil, etc.), ACE inhibitors (e.g., captopril, enalapril, fosinopril, lisinopril, perindopril, quinapril, ramipril, trandolapril, benazepril, etc.), angiotensin II receptor antagonists (e.g., candesartan, eprosartan, irbesartan, losartan, olmesartan, telmisartan, valsartan, etc.), aldosterone receptor antagonists (e.g., eplerenone, spironolactone, etc.), vasodilators (e.g., sodium nitroprusside, hydralazine, etc.), alpha-2 agonists (e.g., clonidine, guanabenz, methyldopa, moxonidine, etc.), adrenergic neuron blockers (e.g., guanethidine, reserpine, etc.), or the like.

In yet another set of embodiments, a composition as discussed herein may be administered to a subject, for example, to improve athletic performance. For example, strenuous exercise may cause oxidative stresses, e.g., due to muscle fatigue. Compositions as discussed herein may be useful to reduce oxidative damage during exercise. In addition, in some cases, xenon may be used to increase production of erythropoietin. This may be useful, for example, to increase red blood cells, e.g., to treat anemic subjects, or improve athletic performance. Without wishing to be bound by any theory, it is believed that xenon may enhance production of HIF1a, which is a transcription factor able to respond to hypoxic conditions. Thus, in some cases, a composition as described herein may be used to increase a subject's physical energy levels, e.g., for improvement in athletic performance. Additionally, in some embodiments, a composition as described herein can be used to treat anemia or other conditions in a subject.

Additionally, in one set of embodiments, a composition as discussed herein may be applied to a subject that is about to be anaesthetized (partially or completely), for example, by applying a suitable anesthetic to the subject (e.g., general or regional anesthetics). The composition may provide, for example, various neuroprotective effects, or other effects such as those described herein. The composition and the anesthetic may be administered to the subject in any suitable order, e.g., simultaneously or sequentially (in any order). In some cases, the subject is conscious while the composition is administered (for example, the subject may drink the composition). In some cases, the anesthetic and the composition are administered proximate in time. For instance, the anesthetic and the composition can be administered such that the subject will be anesthetized while subject to at least some of the effects of the composition (e.g., comprising hydrogen and/or oxygen gas). In some cases, the anesthetic and the composition may be administered within 60 minutes, 45 minutes, 30 minutes, 20 minutes, 15 minutes, 10 minutes, or 5 minutes of each other. Examples of anesthetics that may be administered include, but are not limited to, propofol, sodium thiopental, etomidate, ketamine, sevoflurane, lidocaine, fentanyl, nitrous oxide, isoflurane, or desflurane.

Another set of embodiments of the present invention permit treatment or prevention of various symptoms associated with metabolic conditions or disorders, e.g., diabetes or excessive weight gain. In some embodiments, metabolic conditions generally relate to conditions or disorders that that interfere with the body's metabolism. In some embodiments, metabolic conditions are inherited. Some metabolic disorders can be diagnosed by routine screening tests done at birth. Others are identified only after a child or adult shows symptoms of a disorder. Examples of metabolic conditions, disorders, or diseases contemplated by the present invention include, but are not limited to, obesity, diabetes, metabolic syndrome, impaired glucose tolerance (IGT), hyperglycemia, insulin resistance, dyslipidemia, or the like.

In certain embodiments, compositions provided herein are useful in treating metabolic syndrome, which in some aspects, is defined by The National Cholesterol Education Program criteria, which is defined as the presence of three or more of the following risk factors in the same individual: abdominal obesity or waist circumference greater than 102 cm (40 in) (men) or greater than 88 cm (35 in) (women), serum triglycerides greater or equal to 150 mg/dl, HDL cholesterol less than 40 mg/dl (men) or less than 50 mg/dl (women), systolic blood pressure greater than or equal to 130 mm Hg, diastolic blood pressure greater than or equal to 85 mm Hg, fasting blood glucose greater than or equal to 110 mg/dl. Thus, in some embodiments, the effectiveness of certain compositions, as described herein, is monitored using the above criteria, e.g., by observing a decrease in one or more risk factors over time.

In another set of embodiments, a composition as discussed herein may be administered to a subject to improve metabolism within the subject. In some cases, for instance, there may be antiaging or other positive effects, such as increased muscle growth, bone density, cartilage strength, tendon strength, or the like. In addition, there may be improved metabolism of various systems, such as the kidney, pancreas, gonads, or the like.

One set of embodiments is generally directed to treatment of various inflammatory diseases, such as inflammatory dermatoses, arthritis, osteoarthritis, septic shock, rheumatoid arthritis, or other autoimmune diseases. Without wishing to be bound by any theory, it is believed that xenon may increase removal of selectin PSGL-1 and L-selectin, and thus, xenon may have anti-inflammatory properties, as these selectins are part of the inflammatory response. In addition, xenon may limit injuries such as myocardial, brain, lung and/or kidney injury through inhibition of the N-methyl-d-aspartate (NMDA) receptor, for example, caused by hypothermia, hypoxia, ischemia, oxygen deprivation, oxygen glucose deprivation, or the like, e.g., by limiting glutamate excitotoxicity. In addition, without wishing to be bound by any theory, hydrogen may also exhibit anti-inflammatory effects, for example, by inducing inflammatory cytokines and/or decreasing the expressions of pro-inflammatory factors such as TNF-alpha, IL-6, IL-1-beta, CCL2, IL-10, TNF-gamma, IL-12, ICAM-1, HMGB-1, NF-kB, PGE2, etc. Thus, it is believed that the combination of xenon and hydrogen may have relatively large anti-inflammatory effects, which may be useful for treating various inflammatory diseases such as those discussed herein.

In certain embodiments of the invention, the administration of various compositions of the invention may be designed so as to result in sequential exposures to the composition over a certain time period, for example, hours, days, weeks, months, or years. This may be accomplished, for example, by repeated administrations of a composition of the invention by one or more of the methods described herein. In some cases, compositions may be applied to the subject on a relatively regular or periodic basis; e.g., a subject may drink a container each day, or a two, three, four, or more containers a day, or a container every other day, every third day, every fourth day, etc. Somewhat more irregular schedules are also possible (e.g., a regular number of containers per week or per month, etc.).

Thus, the compositions of the present invention may be administered in multiple doses over extended period of time. For any composition described herein the therapeutically effective amount can be initially determined from animal models. The applied dose can be adjusted based on the relative bioavailability and potency of the administered composition. Adjusting the dose to achieve maximal efficacy based on the methods described above and other methods as are well-known in the art is well within the capabilities of the ordinarily skilled artisan.

When administered to a subject, effective amounts will depend on the particular condition being treated and the desired outcome. A therapeutically effective dose may be determined by those of ordinary skill in the art, for instance, employing factors such as those described herein and using no more than routine experimentation.

In administering the compositions of the invention to a subject, dosing amounts, dosing schedules, routes of administration, and the like may be selected so as to affect known activities of these compositions. Dosages may be estimated based on the results of experimental models, optionally in combination with the results of assays of compositions of the present invention. Dosage may be adjusted appropriately to achieve desired drug levels, local or systemic, depending upon the mode of administration. The doses may be given in one or several administrations per day. Multiple doses per day are also contemplated in some cases to achieve appropriate systemic levels of the composition within the subject or within the active site of the subject.

The dosage may be given in some cases at the maximum amount while avoiding or minimizing any potentially detrimental side effects within the subject. The dosage of the composition that is actually administered is dependent upon factors such as the final concentration desired at the active site, the method of administration to the subject, the efficacy of the composition, the longevity of the composition within the subject, the timing of administration, the effect of concurrent treatments (e.g., as in a cocktail), etc. The dose delivered may also depend on conditions associated with the subject, and can vary from subject to subject in some cases. For example, the age, sex, weight, size, environment, physical conditions, or current state of health of the subject may also influence the dose required and/or the concentration of the composition. Variations in dosing may occur between different individuals or even within the same individual on different days. It may be preferred that a maximum dose be used, that is, the highest safe dose according to sound medical judgment. Preferably, the dosage form is such that it does not substantially deleteriously affect the subject.

Administration of the composition can be alone, or in combination with other therapeutic agents and/or compositions. In certain embodiments of the invention, a composition can be combined with a suitable pharmaceutically acceptable carrier, for example, within a suitable aqueous solution. In general, pharmaceutically acceptable carriers suitable for use in the invention are well-known to those of ordinary skill in the art. As used herein, a "pharmaceutically acceptable carrier" refers to a non-toxic material that does not significantly interfere with the effectiveness of the biological activity of the active composition(s) to be administered, but is used as a formulation ingredient, for example, to stabilize or protect the active composition(s) within the composition before use. The carrier may include one or more compatible solid or aqueous solution fillers, diluents or encapsulating substances which are suitable for administration to a human or other vertebrate animal. The term "carrier" denotes an organic or inorganic ingredient, which may be natural or synthetic, with which one or more compositions of the invention are combined to facilitate the application of the composition. The carrier may be co-mingled or otherwise mixed with one or more compositions of the present invention, and with each other, in a manner such that there is no interaction which would substantially impair the desired pharmaceutical efficacy. Those skilled in the art will know of suitable carriers, such as saline, or will be able to ascertain such, using only routine experimentation.

The formulations of the invention are administered in pharmaceutically acceptable solutions, which may routinely contain pharmaceutically acceptable concentrations of salt, buffering agents, preservatives, compatible carriers, adjuvants, emulsifiers, diluents, excipients, chelating agents, fillers, drying agents, antioxidants, antimicrobials, preservatives, binding agents, bulking agents, silicas, solubilizers, stabilizers and optionally other therapeutic ingredients, that may be used with the active composition. For example, if the formulation is a aqueous solution, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. Those of skill in the art can readily determine the various parameters for preparing and formulating the compositions of the invention without resort to undue experimentation.

In certain embodiments, the containers and compositions described herein are substantially non-toxic. The term "non-toxic" refers to a substance that does not comprise a toxic compound. The term "toxic" refers to a substance showing detrimental, deleterious, harmful, or otherwise negative effects on a subject, tissue, or cell when or after administering the substance to the subject or contacting the tissue or cell with the substance, compared to the subject, tissue, or cell prior to administering the substance to the subject or contacting the tissue or cell with the substance. In certain embodiments, the effect is death or destruction of the subject, tissue, or cell. In certain embodiments, the effect is a detrimental effect on the metabolism of the subject, tissue, or cell. In certain embodiments, a toxic substance is a substance that has a median lethal dose (LD50) of not more than 500 milligrams per kilogram of body weight when administered orally to an albino rat weighing between 200 and 300 grams, inclusive. In certain embodiments, a toxic substance is a substance that has an LD50 of not more than 1,000 milligrams per kilogram of body weight when administered by continuous contact for 24 hours (or less if death occurs within 24 hours) with the bare skin of an albino rabbit weighing between two and three kilograms, inclusive. In certain embodiments, a toxic substance is a substance that has an LC50 in air of not more than 2,000 parts per million by volume of gas or vapor, or not more than 20 milligrams per liter of mist, fume, or dust, when administered by continuous inhalation for one hour (or less if death occurs within one hour) to an albino rat weighing between 200 and 300 grams, inclusive.

A "subject" refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention is directed toward use with humans. In some embodiments, a subject may demonstrate health benefits, e.g., upon administration of the composition.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art.

The following examples illustrate embodiments of certain aspects of the invention. It should be understood that the methods and/or materials described herein may be modified and/or scaled, as known to those of ordinary skill in the art.

Example 1

A container containing a composition is provided. The container comprises glass, which includes $TiO_2$ on an inner wall of the glass. A system comprising a valve configured and designed for the flow of liquid hydrogen is placed into fluidic communication with the container. Liquid hydrogen is flowed through the system such that greater than or equal to 0.1 mg and less than or equal to 5 mg of liquid hydrogen is introduced to the composition and the container is sealed. The liquid hydrogen in the sealed container changes phase into gaseous hydrogen, such that the container is pressurized and such that the gaseous hydrogen is present in the composition in an amount of greater than or equal to 0.1 ppm and less than or equal to 5 ppm.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising: a sealed container formed from glass, the glass comprising at least 10 mass % $TiO_2$, wherein the container contains an aqueous solution comprising dissolved $H_2$ at a concentration of at least 1 ppm and dissolved Xe at a concentration of at least 1 ppm by mass.

2. The article of claim 1, wherein the container has an internal pressure of at least 1 psi greater than atmospheric pressure.

3. The article of claim 1, wherein the aqueous solution comprises dissolved $H_2$ at a concentration of at least 3 ppm.

4. The article of claim 1, wherein at least some of the $TiO_2$ coats a surface of the glass.

5. The article of claim 1, wherein at least some of the $TiO_2$ is embedded in the glass.

6. The article of claim 1, wherein the aqueous solution further comprises flavoring.

7. The article of claim 1, wherein the aqueous solution comprises at least 90% water by mass.

8. The article of claim 1, wherein the glass is substantially transparent.

9. The article of claim 1, wherein the $TiO_2$ catalyzes hydrolysis of water within the container.

10. The article of claim 1, wherein the container is a bottle.

11. A method, comprising: unsealing a sealed container formed from glass, the glass comprising at least 10 mass % $TiO_2$, wherein the container contains an aqueous solution comprising dissolved $H_2$ at a concentration of at least 1 ppm and dissolved Xe at a concentration of at least 1 ppm by mass; and drinking the aqueous solution.

12. The method of claim 11, wherein the sealed container has an internal pressure of at least 1 psi greater than atmospheric pressure.

13. The method of claim 11, wherein the aqueous solution comprises dissolved $H_2$ at a concentration of at least 3 ppm.

14. The method of claim 11, wherein at least some of the $TiO_2$ coats a surface of the glass.

15. The method of claim 11, wherein at least some of the $TiO_2$ is embedded in the glass.

16. The method of claim 11, wherein the aqueous solution comprises at least 90% water by mass.

17. The method of claim 11, wherein the glass is substantially transparent.

18. The method of claim 11, wherein the $TiO_2$ catalyzes hydrolysis of water within the container.

* * * * *